US012655382B2

(12) United States Patent
Hara et al.

(10) Patent No.: US 12,655,382 B2
(45) Date of Patent: Jun. 16, 2026

(54) BACTERIUM, COMPOSITION AND METHOD FOR PRODUCING SAME, AND PREBIOTICS COMPOSITION

(71) Applicant: MORINAGA MILK INDUSTRY CO., LTD., Tokyo (JP)

(72) Inventors: Sakiko Hara, Zama (JP); Toshitaka Odamaki, Zama (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 670 days.

(21) Appl. No.: 17/792,585

(22) PCT Filed: Jan. 19, 2021

(86) PCT No.: PCT/JP2021/001644
§ 371 (c)(1),
(2) Date: Jul. 13, 2022

(87) PCT Pub. No.: WO2021/149672
PCT Pub. Date: Jul. 29, 2021

(65) Prior Publication Data
US 2023/0082222 A1 Mar. 16, 2023

(30) Foreign Application Priority Data
Jan. 20, 2020 (JP) ................................. 2020-007102

(51) Int. Cl.
*C12N 1/205* (2026.01)
*A23L 33/135* (2016.01)
*C12N 1/20* (2006.01)

(52) U.S. Cl.
CPC .............. *C12N 1/20* (2013.01); *A23L 33/135* (2016.08)

(58) Field of Classification Search
None
See application file for complete search history.

(56) References Cited

U.S. PATENT DOCUMENTS

| | | | |
|---|---|---|---|
| 9,763,465 B2 | 9/2017 | Sprenger | |
| 2015/0119360 A1 | 4/2015 | Yamamoto et al. | |
| 2023/0066020 A1* | 3/2023 | Hara ........................ | C12N 1/20 |

FOREIGN PATENT DOCUMENTS

| | | |
|---|---|---|
| CA | 2822500 A1 | 7/2012 |
| CN | 103582426 A | 2/2014 |
| CN | 103582485 A | 2/2014 |
| CN | 103763940 A | 4/2014 |
| CN | 105722409 A | 6/2016 |
| CN | 109414464 A | 3/2019 |
| EP | 3603655 A1 | 2/2020 |
| JP | 07-267866 A | 10/1995 |
| JP | 2015-512936 A | 4/2015 |

| | | |
|---|---|---|
| JP | 2019-218280 A | 12/2019 |
| WO | WO2012/092155 A1 | 7/2012 |
| WO | WO2012/092156 A1 | 7/2012 |
| WO | WO2012/107865 A2 | 8/2012 |
| WO | WO2013/154725 A1 | 10/2013 |
| WO | WO2013/161820 A1 | 10/2013 |
| WO | WO2014/086373 A1 | 6/2014 |
| WO | WO2017/103850 A1 | 6/2017 |
| WO | WO2018/181069 A1 | 10/2018 |
| WO | WO2019/008104 A1 | 1/2019 |
| WO | WO2019/189200 A1 | 10/2019 |
| WO | WO2019/232284 A1 | 12/2019 |
| WO | WO2020/246583 A1 | 12/2020 |

OTHER PUBLICATIONS

Kitaoka, M., "Molecular mechanism on bifidus factor in human milk," Japanese Journal of Lactic Acid Bacteria 2011;22(1):15-25, with English language abstract.
Urashima et al., Milk Science 2008;56(4):155-176, with English language summary.
Kitaoka, Milk Science 2012;61(2):115-124, with English language summary.
Yu, Z.-T. et al., "Utilization of major fucosylated and sialylated human milk oligosaccharides by isolated human gut microbes", Glycobiology, 2013, vol. 23, No. 11, pp. 1281-1292.
Garrido, D. et al., "Comparative transcriptomics reveals key differences in the response to milk oligosaccharides of infant gut-associated bifidobacteria", Sci. Rep., 2015, vol. 5, article No. 13517 (pp. 1-17).
Thongaram, T. et al., "Human milk oligosaccharide consumption by probiotic and human-associated bifidobacteria and lactobacilli", J. Dairy Sci., 2017, vol. 100, No. 10, pp. 7825-7833.
Bunesova, V. et al., "Fucosyllactose and L-fucose utilization of infant Bifidobacterium longum and Bifidobacterium kashiwanohense", BMC Microbiol., 2016, vol. 16, article No. 248 (pp. 1-12).
Idota, T. et al., "Growth-promoting Effects of N-Acetylneuraminic Acid-containing Substances on Bifidobacteria", Biosci. Biotech. Biochem., 1994, vol. 58, No. 9, pp. 1720-1722.
Bondue, P. et al., "Cell-Free Spent Media Obtained from Bifidobacterium bifidum and Bifidobacterium crudilactis Grown in Media Supplemented with 3'-Sialyllactose Modulate Virulence Gene Expression in *Escherichia coli* 0157:H7 and *Salmonella typhimurium*", Front. Microbiol., 2016, vol. 7, article No. 1460 (pp. 1-12).
Asakuma, S. et al., "Physiology of Consumption of Human Milk Oligosaccharides by Infant Gut-associated Bifidobacteria", J. Biol. Chem., 2011, vol. 286, No. 40, pp. 34583-34592.

(Continued)

*Primary Examiner* — Thane Underdahl
*Assistant Examiner* — Mary A Crum
(74) *Attorney, Agent, or Firm* — Cermak & McGowan LLP; Shelly Guest Cermak

(57) ABSTRACT

According to the invention, a novel Bifidobacterial strain having an ability of assimilating two or more kinds of HMO is provided. The strain is selected from the group consisting of *Bifidobacterium longum* subspecies *infantis* (NITE BP-03068), *Bifidobacterium bifidum* (NITE BP-03058) and *Bifidobacterium bifidum* (NITE BP-03067).

9 Claims, No Drawings

(56) References Cited

OTHER PUBLICATIONS

Kim, M. et al., "Bifidogenic prebiotics: comparison between sialyllactose and fucosyllactose and their impact on the bacterial metabolic network", Glycoconj. J., 2015, vol. 32, p. 318; Abst #326.

International Search Report for PCT Patent App. No. PCT/JP2021/001644 (Mar. 9, 2021).

Supplementary Partial European Search Report for Patent App. No. 21744332.4 (dated Feb. 7, 2024).

Ten Bruggencate, S. J. M., et al., "Functional role and mechanisms of sialyllactose and other sialylated milk oligosaccharides," Nutr. Rev. 2014;72(6):377-389.

Extended European Search Report for European Patent App. No. 21744816.6 (dated Jan. 25, 2024).

Underwood, M. A., et al., *"Bifidobacterium longum* subspecies *infantis*: champion colonizer of the infant gut," Pediatric Res., Oct. 10, 2014, XP055311157, US, ISSN: 0031-3998, DOI. 10.1038 pr. 2014.156, pp. 229-235.

Kitaoka, M., Japanese Journal of Lactic Acid Bacteria, vol. 22, No. 1, pp. 15-25, 2011, with English language abstract.

Urashima, T., et al., Milk Science, vol. 56, No. 4, pp. 155-176, 2008, including summary on the first page.

Kitaoka, M., "Molecular mechanism how human milk oligosaccharides stimulate intestinal growth of bifidobacteria" Milk Science 2012;61(2):115-124, including summary on the first page.

Horigome, A., et al., "The Influence of Factors in Breast Milk and the Development of Infant Formula on Infant Gut Microbiota," J. Intest. Microbiol. 2019;33:1-14, including English language abstract.

Ozcan, E., et al., "Inefficient Metabolism of the Human Milk Oligosaccharides Lacto-N-tetraose and Lacto-N-neotetraose Shifts *Bifidobacterium longum* subsp. *infantis* Physiology," Front. Nutr. 2018;5(46):1-18, [online], [retrieved on Feb. 19, 2021].

"Study NCT 03994315: The EFFECT Study: Probiotic and HMO Supplementation in Infants (EFFECT)" published in ClinicalTrials. gov archive, [Online], 2019, [retrieved on Feb. 19, 2021].

International Search Report for PCT Patent App. No. PCT/JP2021/001603 (Mar. 2, 2021).

Chinese Office Action for Application No. 202180009513.7 (dated Oct. 12, 2023) with English language translation thereof.

* cited by examiner

BACTERIUM, COMPOSITION AND METHOD FOR PRODUCING SAME, AND PREBIOTICS COMPOSITION

TECHNICAL FIELD

The present invention relates to a bacterium, a composition, a method for producing the same and a prebiotic composition.

The present application is a U.S. national phase filing of, and claims priority under 35 U.S.C. § 371 to, International Application No. PCT/JP2021/001644, filed Jan. 19, 2021, and claims priority therethrough under 35 U.S.C. § 119 to Japanese Patent Application No. 2020-007102 filed on Jan. 20, 2020 in Japan, and the entireties of which are incorporated here by reference.

BACKGROUND ART

In recent years, many studies on probiotics for the purpose of inhibiting onset of diseases, promoting health, or the like by actively taking bacteria which positively influence animals (also called "good bacteria" below) and regulating the enteric environment and on prebiotics such as components which help the growth of good bacteria have been conducted. While probiotics refer to bacteria which function beneficially in the intestines, prebiotics refer to substances which are selective nutrient sources for the probiotics and which promote the growth thereof. It is known that prebiotics have beneficial effects on human health such as the effect of promoting growth of lactic acid bacteria and *Bifidobacterium* spp., intestinal regulation effect and the effect of preventing-improving inflammatory bowel diseases.

Human milk oligosaccharides (also called "HMOs" below) are contained in breast milk in an amount of 10 to 20 g/L and are said to be a mixture of 130 kinds of oligosaccharide or more. The structures thereof are structures in which fucose and sialic acid are added to 13 kinds of core structure. In human milk, the proportion of fucosylated neutral saccharides is high, and 2'-fucosyllactose, lacto-N-fucopentaose I, lacto-N-difucohexaose I and lacto-N-tetraose are typical. The four kinds of oligosaccharide alone account for ⅓ to ¼ of all the human milk oligosaccharides. Oligosaccharides including lacto-N-biose are called type I, and oligosaccharides including N-acetyllactosamine (LacNAc) are called type II. In human milk, the amounts of lacto-N-tetraose and lacto-N-fucopentaose I, which are type I, are higher than the amounts of lacto-N-neotetraose and lacto-N-fucopentaose III, which are type II. The coexistence of type I and type II and the priority of type I are distinctive features of human milk oligosaccharides which are different from milk oligosaccharides of other species (NPLs 1 and 2).

2'-FL and LNT, which are HMOs contained in breast milk, have the bifidobacteria-growing activity. 2'-FL and LNT are known to act as a growth factor for bifidobacteria by being selectively used by bifidobacteria and are important for the formation of intestinal microbiota in which bifidobacteria are dominant. HMOs can be synthesized and can be used industrially (PTL 1).

Bifidobacteria metabolize some HMOs using the GNB/LNB pathway that is specific to bifidobacteria. Although many of the species commonly found in the human intestinal tract have the pathway, most of the bifidobacteria commonly found in the intestinal tracts of animals other than human and insects do not have the pathway. Typical examples of the bacterial species which can grow using HMOs as the sole carbon source are four bacterial species of *Bifidobacterium longum* subspecies *longum, Bifidobacterium longum* subspecies *infantis, Bifidobacterium breve* and *Bifidobacterium bifidum*, which are bifidobacteria commonly found in infants. In particular, two bacterial species thereof, namely *Bifidobacterium longum* subspecies *infantis* and *Bifidobacterium bifidum*, have been reported to use various HMOs (NPL 3).

CITATION LIST

Patent Literature

PTL 1: WO2014/086373

Non Patent Literature

NPL 1: Japanese Journal of Lactic Acid Bacteria Vol. 22, No. 1, pp 15-25 2011
NPL 2: Milk Science Vol. 56, No. 4, pp 155-176 2008
NPL 3: Milk Science Vol. 61, No. 2, pp 115-124 2012

SUMMARY OF INVENTION

Technical Problem

As described above, in metabolizing HMOs, some of bifidobacteria have no ability or a low ability of assimilating HMOs while some bacteria, such as *Bifidobacterium longum* subspecies *infantis* and *Bifidobacterium bifidum*, have an assimilation property for two or more kinds of HMO.

An object of the invention is to provide a novel Bifidobacterial strain having an ability of assimilating two or more kinds of HMO.

Solution to Problem

First, the invention provides at least one strain selected from (a) to (c) below.
  (a) *Bifidobacterium longum* subspecies *infantis* (NITE BP-03068)
  (b) *Bifidobacterium bifidum* (NITE BP-03058)
  (c) *Bifidobacterium bifidum* (NITE BP-03067)
The strain selected from (a) to (c) has an ability of assimilating 2'-fucosyllactose and one or both of 3'-sialyllactose and lacto-N-tetraose.

Next, the invention provides a composition containing at least one strain selected from (a) to (c).

The composition according to the invention can be a probiotic composition.

The composition according to the invention can be used for at least one use selected from the group consisting of a use for an infant or a small child, a use for an adult and a use for an older adult.

The composition according to the invention can be at least one kind of composition selected from the group consisting of an intestinal regulation composition, a food or drink composition and a nutritional composition.

The composition according to the invention can further contain 2'-fucosyllactose and one or both of 3'-sialyllactose and lacto-N-tetraose.

Moreover, the invention provides a prebiotic composition which is used for promoting the growth of at least one strain selected from (a) to (c) below and in which the composition contains 2'-fucosyllactose and one or both of 3'-sialyllactose and lacto-N-tetraose.

(a) *Bifidobacterium longum* subspecies *infantis* (NITE BP-03068)

(b) *Bifidobacterium bifidum* (NITE BP-03058)

(c) *Bifidobacterium bifidum* (NITE BP-03067)

Furthermore, the invention provides a method for producing a composition containing at least one strain selected from (a) to (c) below.

(a) *Bifidobacterium longum* subspecies *infantis* (NITE BP-03068)

(b) *Bifidobacterium bifidum* (NITE BP-03058)

(c) *Bifidobacterium bifidum* (NITE BP-03067)

Advantageous Effects of Invention

According to the invention, a novel Bifidobacterial strain having an ability of assimilating two or more kinds of HMO can be provided.

The effect described here is not necessarily limited and may also be any of the effects described in the present specification.

DESCRIPTION OF EMBODIMENTS

Embodiments for carrying out the invention are explained below. In this regard, the embodiments explained below show examples of typical embodiments of the present disclosure, and the scope of the invention is not construed as being narrower due to the embodiments. In the present specification, in a numerical range expressed with "a lower limit to an upper limit", the upper limit may be "the value or less" or "less than the value", and the lower limit may be "the value or more" or "more than the value". Moreover, the percentages in the present specification are based on mass unless otherwise specified.

<Novel Bifidobacterial Strain>

The novel Bifidobacterial strain according to the invention is at least one strain selected from (a) to (c) above and can exhibit an ability of assimilating two or more kinds of HMO. Specifically, the strain has an ability of assimilating 2'-fucosyllactose (also called "2'-FL" below) and one or both of 3'-sialyllactose (also called "3'-SL" below) and lacto-N-tetraose (also called "LNT" below). Therefore, the novel Bifidobacterial strain according to the invention can grow easily also in the intestines using 2'-FL and one or both of 3'-SL and LNT.

Bifidobacterial strain have been reported to have various physiological functions, and the functions have been reported to be due to the growth in the intestines and the produced substances (for example, acetic acid). Accordingly, the Bifidobacterial strain of the invention can also be expected to be highly safe and show the generally known efficacies of Bifidobacterial strain in a wide age group. Therefore, the Bifidobacterial strain of the invention can be used for a wide range of compositions (for a food or a drink, for a functional food, for a pharmaceutical product, for feed or the like). Moreover, the Bifidobacterial strain of the invention can be expected to have a probiotic effect and thus can also be used for the purpose of promoting the health, improving the diet, improving the enteric environment, preventing-treating an intestinal infection or the like. Each strain is explained in detail below.

(a) *Bifidobacterium longum* Subspecies *INFANTIS* (NITE BP-03068)

As shown in the Examples described below, the abilities of assimilating 2'-FL, 3'-fucosyllactose (also called "3'-FL" below), LNT and lacto-N-neotetraose (also called "LNnT" below) of *Bifidobacterium longum* subspecies *infantis*

(NITE BP-03068) are each OD0.3 or more, which are excellent, in the <Determination Method of Assimilation Property for Saccharide Source> below.

*Bifidobacterium longum* subspecies *infantis* (NITE BP-03068) is novel *Bifidobacterium longum* subspecies *infantis* and was deposited, as a novel bacterial strain due to the bacteriological properties and features below, for an international deposit on Nov. 20, 2019 to NITE Patent Microorganisms Depositary (NPMD), National Institute of Technology and Evaluation (address: 2-5-8 Kazusakamatari, Kisarazu-shi, Chiba 292-0818, Japan) as a strain of *Bifidobacterium infantis* (accession number: NITE BP-03068). The bacterial strain can be generally acquired from the preservation organization. Here, "*Bifidobacterium infantis*" is reclassified as "*Bifidobacterium longum* subspecies *infantis*" and is synonymous.

(b) *Bifidobacterium bifidum* (NITE BP-03058)

As shown in the Examples described below, the abilities of assimilating 2'-FL, 3'-FL, 3'-SL, 6'-sialyllactose (also called "6'-SL" below), LNT and LNnT of *Bifidobacterium bifidum* (NITE BP-03058) are each OD0.3 or more, which are excellent, in the <Determination Method of Assimilation Property for Saccharide Source> below.

*Bifidobacterium bifidum* (NITE BP-03058) is novel *Bifidobacterium bifidum* and was deposited, as a novel bacterial strain due to the bacteriological properties and features below, for an international deposit on Nov. 8, 2019 to NITE Patent Microorganisms Depositary (NPMD), National Institute of Technology and Evaluation (address: 2-5-8 Kazusakamatari, Kisarazu-shi, Chiba 292-0818, Japan) as a strain of *Bifidobacterium bifidum* (accession number: NITE BP-03058). The bacterial strain can be generally acquired from the preservation organization.

(c) *Bifidobacterium bifidum* (NITE BP-03067)

As shown in the Examples described below, the abilities of assimilating 2'-FL, 3'-FL, 3'-SL, 6'-SL, LNT and LNnT of *Bifidobacterium bifidum* (NITE BP-03067) are each OD0.3 or more, which are excellent, in the <Determination Method of Assimilation Property for Saccharide Source> below.

*Bifidobacterium bifidum* (NITE BP-03067) is novel *Bifidobacterium bifidum* and was deposited, as a novel bacterial strain due to the bacteriological properties and features below, for an international deposit on Nov. 20, 2019 to NITE Patent Microorganisms Depositary (NPMD), National Institute of Technology and Evaluation (address: 2-5-8 Kazusakamatari, Kisarazu-shi, Chiba 292-0818, Japan) as a strain of *Bifidobacterium bifidum* (accession number: NITE BP-03067). The bacterial strain can be generally acquired from the preservation organization.

In the invention, a substantially homogeneous bacterial strain of the bacterial strains explained above can also be used. An example of the substantially homogeneous bacterial strain of the bacterial strains according to the invention is a strain of the same genus and is a bacterial strain in which the base sequence of 16S rRNA gene has an identity of preferably 99.9% or more, more preferably 100% to the base sequence of 16S rRNA gene of the strains and which preferably has the identical bacteriological properties to those of the strains.

In the invention, a mutant of the Bifidobacterial strains can also be used as long as the mutant has a feature for achieving the object of the invention (for example, the feature of having an ability of assimilating 2'-FL and one or both of 3'-SL and LNT). The mutant is preferably a strain which has the identical bacteriological properties to those of a Bifidobacterial strain above and which has an ability of assimilating 2'-FL and one or both of 3'-SL and LNT that is equivalent to or higher than that of the Bifidobacterial strain. Whether or not a mutant has "an ability of assimilating 2'-FL and one or both of 3'-SL and LNT that is equivalent to or higher" than that of a Bifidobacterial strain above can be determined, for example, by the method of the Examples described below.

Such a mutant may be constructed by introduction of a non-artificial mutation to a Bifidobacterial strain above. Moreover, such a mutant may be constructed by introduction of a mutation to the strain through treatment using a mutagen such as UV or constructed by introduction of a mutation to a strain above through various genetic engineering methods.

The bacterial strains specified by the bacterial strain names exemplified above are not limited to the strains deposited or registered at the certain organizations under the bacterial strain names themselves (also called "deposited bacterial strains" below for the convenience of explanation) but include substantially equivalent strains thereof (also called "derived strains" or "induced strains") (the same applies to the bacterial strains below). A "substantially equivalent strain of a deposited bacterial strain above" of the bacterial strain means a strain which belongs to the same species as that of the deposited bacterial strain and which achieves the features of the invention that are equivalent to or higher than those of the deposited bacterial strain. Examples of the substantially equivalent strains of the deposited bacterial strains may be strains derived from the deposited bacterial strains as parent strains. The derived strains include strains bred from the deposited bacterial strains or strains naturally generated from the deposited bacterial strains.

The substantially identical bacterial strains and the derived strains are the following strains.

(1) A bacterial strain which is determined to be the identical bacterial strain by the Randomly Amplified Polymorphic DNA method or the Pulsed-field gel electrophoresis method (described in Probiotics in food/ Health and nutritional properties and guidelines for evaluation 85 Page 43).

(2) A bacterial strain which has genes derived from the deposited bacterial strain only but does not have any exogenous gene and which has a DNA identity of 95% or more (suitably 98% or more).

(3) A strain bred from the bacterial strain (including modification by genetic engineering, a mutation or a spontaneous mutation) and a strain having the identical characters.

<Determination Method of Assimilation Property for Saccharide Source>

A bacterial strain is seeded at 1 v/v % to 200 μL of a MRS (de Man-Rogosa-Sharpe) liquid medium containing a saccharide source and cultured under an anaerobic condition at 37° C. The turbidity (OD660) is measured after 16 hours of culture. The presence or absence of the assimilation property and the degree of the assimilation ability are thus determined. The bacterial strain is determined to have "excellent assimilation property" with a difference with the control of OD660 of 0.3 or more, "more excellent assimilation property" with a difference of 0.4 or more, "still further excellent assimilation property" with a difference of 0.5 or more or "extremely excellent assimilation property" with a difference of 0.6 or more.

The bacterial strains according to the invention can be grown, for example, by culturing the bacterial strains.

The culture method is not particularly limited as long as the Bifidobacterial strain of the invention can be grown, and a method generally used for culturing a Bifidobacterial strain can be used with appropriate modification when necessary. For example, the culture temperature may be 30 to 50° C. and is preferably 35 to 45° C. The strain is preferably cultured under an anaerobic condition and can be cultured, for example, while sending an anaerobic gas such as carbon dioxide gas. Furthermore, the strain may be cultured under a microaerophilic condition such as static liquid culture.

The medium for culturing the Bifidobacterial strain of the invention for the growth is not particularly limited, and a medium which is generally used for culturing a Bifidobacterial strain can be used with appropriate modification when necessary. That is, as a carbon source other than the HMOs, for example, saccharides such as galactose, glucose, fructose, mannose, cellobiose, maltose, lactose, sucrose, trehalose, starch hydrolysate and molasses can be used depending on the assimilation properties. As a nitrogen source, for example, ammonia and ammonium salts or nitrates such as ammonium sulfate, ammonium chloride and ammonium nitrate can be used. Moreover, as an inorganic salt, for example, sodium chloride, potassium chloride, potassium sulfate, magnesium sulfate, calcium chloride, calcium nitrate, manganese chloride or ferrous sulfate can be used. Furthermore, organic components such as peptone, soybean powder, a defatted soybean cake, meat extract and yeast extract may also be used. In addition, as a modified medium, for example, MRS medium can be used.

Preferable assimilation components of the Bifidobacterial strain of the invention are 2'-FL, 3'-SL and LNT. At least 2'-FL is preferably contained, and more preferably, one or both of 3'-SL and LNT are further contained depending on the assimilation ability of each bacterial strain. In addition, HMOs such as 3'-FL, 6'-SL and LNnT can be contained depending on the assimilation ability of each bacterial strain.

2'-FL used in the invention has an effect of promoting the growth of the Bifidobacterial strain of the invention. Moreover, by combining 2'-FL and one or both of 3'-SL and LNT depending on the assimilation ability of each bacterial strain, the effect of promoting the growth of the Bifidobacterial strain of the invention can be exhibited more stably. Furthermore, by combining HMOs such as 3'-FL, 6'-SL and LNnT depending on the assimilation ability of each bacterial strain, the effect of promoting the growth of the Bifidobacterial strain of the invention can be exhibited further stably.

The HMOs used as the assimilation components in the invention may be commercial products, may be prepared from milk or may be obtained by a known method such as organic synthesis and enzymatic treatment. Milk (for example, breast milk, powdered formula, cow's milk or a dairy product) containing the HMOs may also be used. Moreover, a composition obtained by blending the HMOs with milk (for example, cow's milk, powdered formula or liquid formula) (that is, milk containing the HMOs) may also be used.

As the HMOs which can be used as the assimilation components in the invention, 2'-FL is preferably contained, and more preferably, one or both of 3'-SL and LNT are further contained depending on the assimilation ability of each bacterial strain. In addition, further preferably, 3'-FL, 6'-SL and LNnT are further contained depending on the assimilation ability of each bacterial strain. In addition to the HMOs, general examples of HMOs include 3-difucosyllactose, 3-fucosyl-3'-sialyllactose, lacto-N-fucopentaose I, lacto-N-fucopentaose II, lacto-N-fucopentaose III, lacto-N-fucopentaose V, lacto-N-difucosylhexaose I, lacto-N-difucosylhexaose II, lacto-N-sialylpentaose, LSTa, LSTb and LSTc. The oligosaccharides of the HMOs can be obtained by a known production method. In the invention, at least one kind of human milk oligosaccharide selected from the group consisting thereof can also be used.

<Prebiotics for Promoting Growth of Bacterium of *Bifidobacterium* of Invention>

2'-FL and one or both of 3'-SL and LNT above have an effect of promoting the growth of a Bifidobacterial strain shown in (a) to (c) above and can be used as prebiotics. Moreover, depending on the assimilation ability of each bacterial strain, one kind of HMOs such as 3'-FL, 6'-SL and LNnT alone or a combination of two or more kinds thereof can also be used. In addition, the production can be conducted appropriately using an optional component suitable for the use by a known production method suitable for the use.

The used amounts or the contained amounts of the HMOs such as 2'-FL, 3'-SL, LNT, 3'-FL, 6'-SL and LNnT in the prebiotic composition of the invention, based on 100 parts by mass of the Bifidobacterial strain shown in (a) to (c) above, are each preferably 1 to 1,000,000 parts by mass, more preferably 10 to 10,000 parts by mass.

When the prebiotic is used, a beneficial probiotic effect on human health of the Bifidobacterial strain shown in (a) to (c) above, such as intestinal regulation effect, the effect of promoting mineral absorption and the effect of preventing-improving an inflammatory bowel disease, can also be expected.

<Composition Containing Bacterium of *Bifidobacterium* of Invention>

The composition of the invention has meanings including a probiotic composition, a food or drink composition, a pharmaceutical composition and the like. Moreover, the composition of the invention is suitably a probiotic composition.

The composition containing a Bifidobacterial strain shown in (a) to (c) above may be used for human as a subject of application or a non-human animal (suitably a mammal). Human or a pet is preferable, and human is more preferable. The subject to which the invention is applied is not particularly limited as long as the subject wishes a probiotic effect, and examples thereof include an infant, a small child, a child, an adult, a healthy individual, a middle-aged person, an older adult and an individual with poor enteric environment. In particular, the invention is preferably used for at least one use selected from the group consisting of a use for an infant or a small child, a use for an adult and a use for an older adult.

Because the Bifidobacterial strains shown in (a) to (c) above used in the invention are derived from human, thus have less side-effects and are highly safe, the strains can be taken continuously for a long period. Moreover, the strains can be used for products in a wide range of uses such as a pharmaceutical product and a food or a drink. The composition of the invention can also be used effectively for a symptom or a disease which can be prevented, improved or treated by probiotics.

In this manner, the Bifidobacterial strains shown in (a) to (c) above can be contained in the probiotic composition as an active ingredient, and the Bifidobacterial strains shown in (a) to (c) above can also be used for the manufacture of such a formulation, such a composition or the like. Moreover, the Bifidobacterial strains shown in (a) to (c) above can also be used as bacteria for probiotics.

The Bifidobacterial strain of the invention can be used directly. The Bifidobacterial strain of the invention can also be used after mixing with a general carrier, diluent or the like which is physiologically acceptable or acceptable for a pharmaceutical product, a food or a drink.

The administration or the intake of the Bifidobacterial strain shown in (a) to (c) above is preferably intake for at least one week, more preferably continuous intake for at least four weeks, further preferably daily intake.

The amount of the Bifidobacterial strain shown in (a) to (c) above used is not particularly restricted due to the high safety but is, for example, preferably $1\times10^6$ to $1\times10^{12}$ CFU/kg body weight/day, more preferably $1\times10^7$ to $1\times10^{11}$ CFU/kg body weight/day, further preferably $1\times10^8$ to $1\times10^{10}$ CFU/kg body weight/day. The used amount (dosage) per individual (body weight) is preferably $10^7$ to $10^{14}$ CFU/day, more preferably $10^8$ to $10^{13}$ CFU/day, further preferably $10^9$ to $10^{12}$ CFU/day. In the invention, CFU means the colony forming unit and indicates the colony forming unit. When the bacterium is a dead bacterium, CFU can be replaced with cells.

The amount of the Bifidobacterial strain shown in (a) to (c) above used is preferably 0.01 to 100 mL/body weight kg/day, more preferably 0.1 to 10 mL/body weight kg/day.

<Pharmaceutical Composition>

The pharmaceutical composition of the invention is not particularly restricted as long as the pharmaceutical composition contains a Bifidobacterial strain shown in (a) to (c) above. The pharmaceutical composition can also be used as an intestinal regulation composition or the like containing a Bifidobacterial strain shown in (a) to (c) above.

As the pharmaceutical composition of the invention, a Bifidobacterial strain shown in (a) to (c) above may be used directly or used after blending a physiologically acceptable liquid or solid carrier for formulation and forming into a drug.

The pharmaceutical composition of the invention contains, as an active ingredient, a Bifidobacterial strain shown in (a) to (c) above, which can be obtained from human intestines as an oral composition component, and thus can be administered also to a patient with various diseases without worries. Moreover, because the Bifidobacterial strain also exist in animal intestines, the invention is not expected to easily cause side-effects even when the invention is continuously administered for a long period. Furthermore, the Bifidobacterial strain can be administered to an infant, a small child and a child safely. Therefore, the invention is also suitable for prevention, improvement and/or treatment of a disease of an infant, a small child or a child or a symptom thereof.

The invention may be used for therapeutic purpose or may be used for non-therapeutic purpose.

The "non-therapeutic purpose" is a concept which does not include medical practice, namely treatment of a human body by therapy. Examples thereof include health promotion, beauty treatment and the like.

The "improvement" means: improvement of a disease, a symptom or the condition; prevention or delay of deterioration of a disease, a symptom or the condition; or reversal, prevention or delay of progress of a disease or a symptom.

The "prevention" means prevention or delay of the onset of a disease or a symptom in the subject of the application or reduction of the risk of a disease or a symptom of the subject of the application.

The dosage form of the pharmaceutical composition of the invention is not particularly restricted, and specifically, examples include tablets, pills, powder, liquid preparation, suspensions, emulsions, granules, capsules, syrups, suppositories, injections, ointment, patches, eye drops, nasal drops and the like. Moreover, for the formulation, an additive which is generally used as a carrier for formulation, such as excipients, binders, disintegrating agents, lubricants, stabilizers, flavoring agents, diluents, surfactants and solvents for injection, can be used.

For the formulation, a component which is generally used for formulation, such as excipients, pH-adjusting agents, colorants and corrigents, can be used for the pharmaceutical composition according to the invention. As long as the effects of the invention are not impaired, a component having the effect of preventing, improving and/or treating a disease or a symptom which is known or will be found in the future and which is relevant to the invention can also be used in the pharmaceutical composition according to the invention.

In addition, the formulation can be conducted by an appropriate known method depending on the dosage form. The formulation may also be conducted by appropriately blending a carrier for formulation.

The amount of the Bifidobacterial strain shown in (a) to (c) above contained in the pharmaceutical composition of the invention is appropriately determined based on the dosage form, the usage, the age of the patient, the gender, the type of disease, the degree of the disease, the other conditions and the like but is generally preferably in the range of $1\times10^6$ to $1\times10^{12}$ cfu/g or $1\times10^6$ to $1\times10^{12}$ cfu/mL, more preferably in the range of $1\times10^7$ to $1\times10^{11}$ cfu/g or $1\times10^7$ to $1\times10^{11}$ cfu/mL. When the Bifidobacterial strain shown in (a) to (c) above is a dead bacterium, cfu/g or cfu/mL can be replaced with cells/g or cells/mL.

The timing of administration of the pharmaceutical composition of the invention is not particularly limited, and the timing of administration can be appropriately chosen according to the method for treating the subject symptom or disease. The pharmaceutical composition may be administered prophylactically or used for a maintenance therapy. Moreover, the form of administration is preferably determined based on the formulation form, the age of the patient, the gender, the other conditions, the degree of the symptom of the patient or the like. In this regard, in all the cases, the pharmaceutical composition of the invention can be administered once a day or in separate portions and may be administered once in several days or in several weeks.

<Food or Drink Composition>

The food or drink composition of the invention may be produced by adding a Bifidobacterial strain shown in (a) to (c) above to a known food or a known drink, or a new food or drink composition can be produced by mixing a Bifidobacterial strain shown in (a) to (c) above into materials of a food or a drink.

The food or drink composition of the invention is not particularly restricted as long as a Bifidobacterial strain shown in (a) to (c) above is contained, and examples of the food or drink composition include: drinks such as soft drinks, carbonated drinks, nutritional drinks, fruit juices and lactic acid bacteria beverages (including concentrated undiluted solutions of the drinks and powders for preparation thereof); frozen desserts such as ice creams, sherbets and shaved ice; confectioneries such as sweets, candies, chewing gums, chocolates, tablet candies, snacks, biscuits, jellies, jams, creams and baked sweets; dairy products such as processed milk, milk beverages, fermented milk, drink yogurts and butter; breads; liquid foods such as enteral nutrition products and porridge, baby foods, liquid formula or sport drinks; and other functional foods. Moreover, the food or the drink may be a supplement and may be, for example, a supplement in the tablet form. In the case of a supplement, a Bifidobacterial strain shown in (a) to (c)

above can be taken while the amount of meals and the calorie intake per day are not affected by other foods.

In the food or drink composition in the invention, a component which has the probiotic effect or a component which supplements the probiotic effect can be used as long as the effects of the invention are not impaired. For example, the food or drink composition in the invention can be prepared by combining a Bifidobacterial strain shown in (a) to (c) above with a component such as: proteins such as whey protein, casein protein, soybean protein and pea protein or mixtures or decomposition products thereof; amino acids such as leucine, valine, isoleucine and glutamine; vitamins such as vitamin B6 and vitamin C; creatine; citric acid; and fish oil.

The food or drink composition defined in the invention can also be provided-sold as a food or a drink with a label with use of probiotics or the like (including a health use). Moreover, the food or drink composition can be provided-sold with a label for "those who wish to lead a life with the Bifidobacterial strain", "those who want to improve the enteric environment", "those who want to correct the gut condition", "those who want to form a good enteric environment" or the like as the subject of the consumption of the food or the drink.

The "labeling" act includes all the acts for informing a consumer of the use, and all the expressions which can remind of cause to guess the use are the "labeling" acts of the invention, regardless of the purposes of labeling, the contents of labeling, the objects to be labeled, the media and the like.

The "label" is preferably with an expression which allows a consumer to directly recognize the use. Specific examples include an act of transferring an article in which the use is described on a product regarding the food or the drink or packaging of a product, delivering such an article, displaying such an article for transfer or delivery or importing such an article, an act of displaying or distributing an advertisement of a product, a price list or a business document with a description of the use thereon or providing information with such contents with a description of the use by an electromagnetic method (internet or the like) and another act.

The content of the label is preferably a label approved by the administration or the like (for example, a label approved based on a system provided by the administration and provided in the form based on the approval or the like). It is preferable to label with such a content on packaging, a container, a catalogue, a brochure, an advertisement material in a sales site such as POP, other documents or the like.

The "labels" also include labels with health foods, functional foods, enteral nutrition products, food for special dietary uses, food with health claims, foods for specified health uses, foods with nutrient function claims, foods with function claims, quasi-drugs and the like. In particular, the labels are labels approved by the Consumer Affairs Agency, such as labels approved by the systems for foods for specified health uses, foods with nutrient function claims or foods with function claims or by a similar system. Specific examples include a label with foods for specified health uses, a label with qualified foods for specified health uses, a label indicating influence on the structure and the function of a body, a label with reduction of disease risk or a label with a scientifically grounded function. More specifically, typical examples include labels with food for specified health uses (especially labels with health uses) provided by the Cabinet Office Ordinance on Labeling Permission for Special Dietary Uses under the Health Promotion Act (Cabinet Office Ordinance No. 57 on Aug. 31, 2009) and similar labels.

The amount of the Bifidobacterial strain shown in (a) to (c) above contained in the food or drink composition of the invention is appropriately determined based on the form of the food or drink composition but is generally preferably in the range of $1\times10^6$ to $1\times10^{12}$ cfu/g or $1\times10^6$ to $1\times10^{12}$ cfu/mL in the food or the drink, more preferably in the range of $1\times10^7$ to $1\times10^{11}$ cfu/g or $1\times10^7$ to $1\times10^{11}$ cfu/mL.

The food or drink composition according to the invention can be used as a nutritional composition. In the invention, the "nutritional composition" refers to a food or a drink which is orally taken. The kind of the nutritional composition which can be used in the invention is not particularly limited but is preferably a formula, a liquid food or the like, more preferably a formula. The subject of the intake may be an infant, a small child, a child or an adult but is preferably an infant or a small child.

The formulas include a powdered formula and a liquid formula.

The powdered formula is defined by the Ministerial Ordinance Concerning Compositional Standards, etc. for Milk and Milk Products as "those obtained by processing raw milk, cow's milk, certified milk or a food produced therefrom as a raw material or using such a material as a major raw material, adding nutrients necessary for infants and small children and processing into powder".

The liquid formula is defined by the Ministerial Ordinance as "those obtained by processing raw milk, cow's milk, certified milk or a food produced therefrom as a raw material or using such a material as a major raw material, adding nutrients necessary for infants and small children and processing into liquid".

The formulas also include those which contain a nutrient component such as proteins, oils and fats, carbohydrates, minerals and vitamins and which are processed into powder or liquid.

The formulas further include "a powdered infant formula", "a liquid infant formula" and "a powdered formula for pregnant and parturient women and nursing mothers" of the food for special dietary uses provided by the Health Promotion Act and also include the forms of a powdered infant formula for infants and small children for infants of the age of 0 to 12 months, follow-up milk for infants and younger children of the age of 6 to 9 months or older (until the age of 3 years), a powdered infant formula for low birthweight infants for newborns with a body weight at birth less than 2500 g (low birthweight infants), a formula for treatment of infants and small children with sickness such as milk allergy and lactose intolerance, a powdered infant formula for small children, nutritional powder for adults, nutritional powder for the older adults and the like.

The food or drink composition (including a nutritional composition) according to the invention can also be applied to food with health claims or food for the ill. The system for food with health claims has been established not only for general foods but also for foods in the form of tablets, capsules and the like, in view of the trends inside and outside of Japan and also considering the consistency with the existing system for foods for specified health uses. The system includes two types, namely foods for specified health uses (individual approval system) and foods with nutrient function claims (standard regulation system).

<Production Method of Composition>

The method for producing the composition of the invention is explained below. In the method for producing the composition of the invention, the step of adding a Bifidobacterial strain shown in (a) to (c) above may be conducted at any stage in the production steps of the composition.

An example of the method for producing the composition is a method for producing the composition including the step A and the step B below.

Step A: a step of culturing a Bifidobacterial strain shown in (a) to (c) above in a medium and thus obtaining a culture or a product containing the Bifidobacterial strain shown in (a) to (c) above Step B: a step of subjecting the culture or the product to drying and thus obtaining bacterial powder or a dried product The form of the Bifidobacterial strain shown in (a) to (c) above or the culture containing the same is not particularly limited and may be liquid or solid, but the form is suitably a dried form (for example, bacterial powder or a dried culture) in view of easiness of handling during the production and during the storage. Moreover, the culture may be, as described above, bacterial cells from which the culture solution has been separated, a culture containing bacterial cells, a culture from which bacterial cells have been removed or the like.

The drying method is not particularly limited, either, as long as the effects of the invention are not impaired but may be spray drying method, retort sterilization method, lyophilization method, UHT pasteurization method, pressurized sterilization method, high-pressure steam sterilization method, dry heat sterilization method, flow steam sterilization method, electromagnetic wave sterilization method, electron beam sterilization method, high-frequency sterilization method, radiation sterilization method, ultraviolet sterilization method, ethylene oxide gas sterilization method, hydrogen peroxide gas plasma sterilization method, chemical sterilization method (alcohol sterilization method, formalin fixation method or electrolyzed water treatment method) or the like. In the invention, lyophilization or spray drying is suitable.

The bacterial cells may be homogenized, and the homogenate may be bacterial cells obtained by homogenizing the living bacterium, bacterial cells obtained by homogenizing the dead bacteria or bacterial cells which have been subjected to heating, lyophilization or the like after homogenization.

Of these, the culture is suitably subjected to lyophilization to increase the viability, and the culture is suitably subjected to spray drying to increase the production efficiency.

An example of the method for producing the composition is a method for producing the composition including at least the step C or the step D.

Step C: a step of mixing a Bifidobacterial strain shown in (a) to (c) above and a prebiotic Step D: a step of mixing a Bifidobacterial strain shown in (a) to (c) above and a milk component As the Bifidobacterial strain shown in (a) to (c) above here, a composition containing the Bifidobacterial strain shown in (a) to (c) above may be used. Moreover, the composition may further contain a probiotic such as other Bifidobacterial strains and lactic acid bacteria.

When the prebiotic is mixed, the step may be any of the production steps.

The milk component is suitably powder and is more suitably mixed with bacterial powder of the Bifidobacterial strain shown in (a) to (c) above.

The milk component is not particularly limited as long as the effects of the invention are not impaired, but examples thereof include cow's milk, buffalo's milk, sheep's milk, goat's milk, mare milk, skim milk, concentrated skim milk, skim milk powder, concentrated milk, whole milk powder, cream, butter, buttermilk, condensed milk, a milk protein and the like. One, two or more kinds selected from the group consisting thereof can be used. The milk protein is not particularly limited, but examples thereof include whey, casein, hydrolysates thereof and the like. One, two or more kinds selected from the group consisting thereof can be used. Of the milk components, a component derived from cow's milk is suitable.

Regarding the hydrolysates, a whey hydrolysate, a casein hydrolysate or the like can be produced by hydrolyzing the milk component (suitably a milk protein). Examples of the hydrolysis include acid·alkali hydrolysis, enzymatic hydrolysis and the like. Of these, enzymatic hydrolysis is suitable, and a proteolytic enzyme is suitable as the enzyme. Examples of the proteolytic enzyme include protease, trypsin, chymotrypsin, plasmin, pepsin, papain, peptidase, aminopeptidase and the like. The pH during the hydrolysis reaction is appropriately adjusted to the optimum pH of the enzyme used, and the hydrolysis reaction can be conducted, for example, at pH 2 to 6 or the like. The temperature during the hydrolysis reaction is not particularly limited but is generally suitably in the range of 30 to 60° C., and the reaction period is preferably 2 to 10 hours.

When a supplement or tablets are produced as the composition of the invention, a step of mixing a culture containing a Bifidobacterial strain shown in (a) to (c) above and an excipient or the like and thus obtaining a mixture and a step of forming into a certain shape can be included. The forming step is, for example, tableting or the like, and an example of tableting is obtaining tablets by compression forming of a powder or granulated mixture or the like.

Furthermore, an example of the method for producing the composition of the invention is a method for producing a fermented food or drink (suitably a fermented milk) containing a Bifidobacterial strain shown in (a) to (c) above.

A step of adding the bacterial powder obtained by the production method described above to a fermented milk raw material and obtaining a fermented milk containing a Bifidobacterial strain shown in (a) to (c) above using the Bifidobacterial strain is conducted. Alternatively, a step of mixing the bacterial powder and a fermented milk and thus obtaining a fermented milk containing a Bifidobacterial strain shown in (a) to (c) above is conducted. Regarding the bacterial cell amount of the strain of the invention in the composition, the fermentation conditions and the blending amount are adjusted to achieve a certain bacterial cell amount. As a result, a fermented food or drink (suitably a fermented milk or a fermented product) containing a Bifidobacterial strain shown in (a) to (c) above can be provided.

EXAMPLES

The invention is explained in further detail below based on Examples. In this regard, the Examples explained below show examples of typical Examples of the invention, and the scope of the invention is not construed as being narrower due to the Examples.

Bacterial solutions of four Bifidobacterial strains possessed by Morinaga Milk Industry Co., Ltd. (called "candidate bacterial strains" below) were seeded at 1 v/v % to 200 µL of a medium after 16 hours of degassing and cultured under an anaerobic condition at 37° C. As the media, MRS (de Man-Rogosa-Sharpe) liquid media (composition: Table 2) in which the saccharide source was changed to the six kinds of human milk oligosaccharide (manufactured by Jennewein Biotechnologie GmbH) shown in Table 1 were produced. The turbidities (OD660) after 16 hours of culture were measured, and the presence or absence of the assimilation property and the degree of the assimilation ability were determined. The bacterial strains were determined to have "excellent assimilation property" with OD660 of 0.3 or more, "more excellent assimilation property" with OD660 of 0.5 or more or "extremely excellent assimilation property" with OD660 of 0.8 or more.

As controls, *Bifidobacterium breve* (JCM 1192) and *Bifidobacterium longum* subspecies *infantis* (ATCC 15697) were used. The averages of measured turbidity (OD660) values after 16 hours of culture are shown in Table 1.

TABLE 1

| | | | | | | |
| Turbidity (OD660) After 16 Hours of Culture | | | | | | |
| | 2'-FL | 3'-FL | 3'-SL | 6'-SL | LNT | LNnT |
| *Bifidobacterium breve* JCM 1192 | 0.272 | — | — | — | — | — |
| *Bifidobacterium longum* subspecies *infantis* ATCC 15697 | 0.4955 | 0.6935 | 0.1545 | 0.1675 | 0.9795 | 0.9895 |
| *Bifidobacterium longum* subspecies *infantis* NITE BP-03068 (candidate bacterial strain 1) | 0.5625 | 0.6445 | 0.158 | 0.1755 | 1.0610 | 0.9625 |
| *Bifidobacterium bifidum* NITE BP-03058 (candidate bacterial strain 2) | 0.704 | 0.5625 | 0.571 | 0.63 | 1.1515 | 1.085 |
| *Bifidobacterium bifidum* NITE BP-03067 (candidate bacterial strain 3) | 0.671 | 0.393 | 0.469 | 0.4605 | 1.0825 | 1.041 |

TABLE 2

| MRS Composition | |
| --- | --- |
| BBL Polypeptone (manufactured by BD Bioscience) | 10 g |
| Bacto Beef Extract (Desicated, manufactured by BD Bioscience) | 10 g |
| Bacto Yeast Extract (manufactured by BD Bioscience) | 5 g |
| Polyoxyethylene sorbitan monooleate (manufactured by Nacalai) | 1 g |
| Dipotassium hydrogenphosphate (manufactured by Kokusan Chemical Co., Ltd.) | 2 g |
| Sodium acetate (manufactured by Wako Pure Chemical Industries, Ltd.) | 5 g |
| Diammonium hydrogen citrate (manufactured by Wako Pure Chemical Industries, Ltd.) | 2 g |
| Magnesium sulfate heptahydrate (manufactured by Wako Pure Chemical Industries, Ltd.) | 0.2 g |

TABLE 2-continued

| MRS Composition | |
| --- | --- |
| Manganese(II) sulfate pentahydrate (manufactured by Wako Pure Chemical Industries, Ltd.) | 0.05 g |
| Distilled water | 800 mL |
| SW (added later) | 200 mL |
| Total | 1000 mL |
| pH | 6.5 |

From the above results, it was found that the four candidate bacterial strains all had higher assimilation property for 2'-FL than the controls and that some bacterial strains also assimilated other human milk oligosaccharides.

Production Examples

Production Examples of the composition, the pharmaceutical composition, the fermented milk, the powdered formula and the food or drink composition of the invention are shown below, but the composition of the invention is not limited thereto.

Production Example 1

*Bifidobacterium longum* subspecies *infantis* (NITE BP-03068) is added to 3 mL of MRS liquid medium and anaerobically cultured at 37° C. for 16 hours, and then the culture solution is concentrated and lyophilized to obtain lyophilized powder of the bacterium (bacterial powder). The bacterial powder, a whey protein concentrate (WPC) and prebiotics (2'-FL and LNT) are uniformly mixed, and thus a composition is obtained. The composition in an amount of 20 g is dissolved in 200 g of water, and thus a composition containing *Bifidobacterium longum* subspecies *infantis* (NITE BP-03068) is obtained.

Production Example 2

*Bifidobacterium bifidum* (NITE BP-03058) is added to 3 mL of MRS liquid medium and anaerobically cultured at 37° C. for 16 hours, and then the culture solution is concentrated and lyophilized to obtain lyophilized powder of the bacterium (bacterial powder). The bacterial powder, dry powder of a milk protein concentrate (MPC480, manufactured by Fonterra Co-operative Group, protein content of 80 mass %, casein protein:whey protein=about 8:2) and prebiotics (2'-FL, 3'-SL and LNT) are uniformly mixed, and thus a composition is obtained. The composition in an amount of 20 g is dissolved in 200 g of water, and thus a composition containing *Bifidobacterium bifidum* (NITE BP-03058) is obtained.

Production Example 3

*Bifidobacterium bifidum* (NITE BP-03067) is added to 3 mL of MRS liquid medium and anaerobically cultured at 37° C. for 16 hours, and then the culture solution is concentrated and lyophilized to obtain lyophilized powder of the bacterium (bacterial powder) containing *Bifidobacterium bifidum* (NITE BP-03067). Next, prebiotics (2'-FL, 3'-SL and LNT) and crystalline cellulose are introduced into an agitation granulator and mixed. Then, purified water is added for granulation, and the granules are dried to obtain granules (a pharmaceutical composition) containing a fermented component of the bacterium and the prebiotics and containing the excipient. In this manner, granules containing *Bifidobacterium bifidum* (NITE BP-03067) can be obtained.

Production Example 4

A production method of a fermented milk containing *Bifidobacterium bifidum* (NITE BP-03067) is shown below.

First, a raw milk material, water according to the need, other components and the like are mixed, preferably homogenized and heat sterilized. The homogenization and the heat sterilization can be conducted by general methods. A lactic acid bacterium starter is added (seeded) to the heat sterilized prepared milk solution, and the solution is kept at a certain fermentation temperature and fermented to obtain a fermented product. Through fermentation, curd is formed.

As the lactic acid bacterium starter, for example, lactic acid bacteria which are generally used for yogurt production, such as *Lactobacillus bulgaricus, Lactococcus lactis* and *Streptococcus thermophilus*, can be used. When the pH reaches the target value, the formed curd is crushed by stirring and cooled to 10° C. or lower, and a fermented product is thus obtained. By cooling to 10° C. or lower, the activity of the lactic acid bacterium can be reduced, and the formation of an acid can be inhibited.

Next, the fermented product obtained by the fermentation step is heat treated, and a fermented product after the heating (a fermented product after the heat treatment) is thus obtained. By appropriately heating the fermented product, the formation of an acid by the lactic acid bacterium in the fermented product after the heating can be inhibited. As a result, a decrease in pH during the subsequent production step and/or during the storage of the concentrated fermented milk containing the Bifidobacterial strain can be inhibited, and as a result, the viability of the Bifidobacterial strain can be improved.

Next, *Bifidobacterium bifidum* (NITE BP-03067) and prebiotics (2'-FL, 3'-SL and LNT) are added to the fermented product after the heating obtained by the heat treatment step. The amount of *Bifidobacterium bifidum* (NITE BP-03067) added, relative to the fermented product after the heating, is preferably $1 \times 10^7$ to $1 \times 10^{11}$ CFU/mL, more preferably $1 \times 10^8$ to $1 \times 10^{10}$ CFU/mL. When the *Bifidobacterium bifidum* (NITE BP-03067) is a dead bacterium, CFU/mL can be replaced with cells/mL.

After adding *Bifidobacterium bifidum* (NITE BP-03067) and the prebiotics to the fermented product after the heating, the mixture is concentrated. The concentration step can be conducted appropriately using a known concentration method. For example, centrifugation method or membrane separation method can be used.

Through the centrifugation method, the whey in the product to be concentrated (the fermented product after the heating containing the Bifidobacterial strain and the prebiotics) is removed, and a concentrated fermented milk which has an increased solid content concentration and which contains the Bifidobacterial strain and the prebiotics is obtained.

The fermented milk containing *Bifidobacterium bifidum* (NITE BP-03067) obtained as described above can be produced.

Production Example 5

A production method of a powdered formula containing *Bifidobacterium longum* subspecies *infantis* (NITE BP-03068) is shown below.

In 300 kg of warm water, 10 kg of desalted cow's milk whey protein powder (manufactured by MILEI GmbH), 6 kg of cow's milk casein powder (manufactured by Fonterra Co-operative Group), 48 kg of lactose (manufactured by MILEI GmbH), 920 g of a mineral mixture (manufactured by Tomita Pharmaceutical Co., Ltd), 32 g of a vitamin mixture (manufactured by Tanabe Seiyaku Co., Ltd.), 500 g of lactulose (manufactured by Morinaga Milk Industry Co., Ltd.), 500 g of raffinose (manufactured by Nippon Beet Sugar Manufacturing Co., Ltd.) and 900 g of galactooligo-saccharide syrup (manufactured by Yakult Pharmaceutical Industry Co., Ltd.) were dissolved and further heated and dissolved at 90° C. for 10 minutes, and after adding 28 kg of modified fats (manufactured by Taiyo Yushi Corp.), the mixture was homogenized. Then, after sterilization and concentration steps, the mixture was spray dried, and about 95 kg of a powdered formula was thus prepared. To the powdered formula, 100 g of bacterial powder of *Bifidobacterium longum* subspecies *infantis* (NITE BP-03068) (1.8× $10^{11}$ cfu/g, manufactured by Morinaga Milk Industry Co., Ltd.) triturated in starch is added, and about 95 kg of a powdered formula containing the Bifidobacterial strain and oligosaccharides is thus prepared. When the obtained powdered formula is dissolved in water and when a formula solution having a total solid content concentration as a standard formula concentration of 14% (w/V) is obtained, $2.7×10^9$ cfu/100 mL can be obtained as the bacterial count of the Bifidobacterial strain in the formula solution.

By taking or administering the powdered formula containing *Bifidobacterium longum* subspecies *infantis* (NITE BP-03068) obtained as described above, human enteric environment can be improved.

Production Example 6

A production method of a food for improving enteric environment containing *Bifidobacterium bifidum* (NITE BP-03058) is shown below.

*Bifidobacterium bifidum* (NITE BP-03058) is added to 3 mL of MRS liquid medium and anaerobically cultured at 37° C. for 16 hours, and then the culture solution is concentrated and lyophilized to obtain lyophilized powder of the bacterium (bacterial powder) and to obtain the composition of the invention. The bacterial powder of the invention can be added to a cellulose-rich food (vegetables, salads or the like) and cooked, and thus the composition of the invention can also be obtained.

Alternatively, the bacterial powder is taken at a meal, before a meal, during a meal or after a meal. Because dietary fibers are automatically taken with a regular diet (a diet with staple food, a side dish and a main dish), an effect of improving the enteric environment of an adult can be expected when the dry bacterial powder product of the invention is taken together during a meal.

When the food for improving enteric environment of the invention is continuously taken by a person feeling a problem with the intestines, such as constipation and diarrhea, a higher effect of improving enteric environment can be expected.

From the above points, the Bifidobacterial strain of the invention, which has an ability of assimilating 2'-FL and 3'-SL or LNT, the composition containing the Bifidobacterial strain and the composition for promoting the growth of the Bifidobacterial strain can help the growth of the Bifido-bacterial strain in the intestines and can be effectively used for the formation of an excellent intestinal microbiota, the improvement of enteric environment or the like.

The invention claimed is:

1. A spray-dried or lyophilized powder of a bacterial strain selected from the group consisting of:
   (a) *Bifidobacterium longum* subspecies *infantis* NITE BP-03068,
   (b) *Bifidobacterium bifidum* NITE BP-03058 and
   (c) *Bifidobacterium bifidum* NITE BP-03067;
wherein said strain is able to assimilate 2'-fucosyllactose, and one or both of 3'-sialyllactose and lacto-N-tetraose.

2. A composition containing the spray-dried or lyo-philized powder of a bacterial strain according to claim 1, wherein the composition is selected from the group consist-ing of a tablet, pill, emulsion, ointment, powder, granule, capsule, and syrup.

3. The composition according to claim 2, wherein the composition is a probiotic composition, and wherein the amount of the bacterial strain in the composition is in the range of $1×10^6$ to $1×10^{12}$ cfu/g or $1×10^6$ to $1×10^{12}$ cfu/ml.

4. The composition according to claim 2, wherein the composition is formulated for a population selected from the group consisting of an infant, a small child, an adult, and an older adult, and wherein the amount of the bacterial strain in the composition is in the range of $1×10^6$ to $1×10^{12}$ cfu/g or $1×10^6$ to $1×10^{12}$ cfu/ml.

5. The composition according to claim 2, wherein the composition is selected from the group consisting of an intestinal regulation composition, a food composition, and a nutritional composition, and wherein the amount of the bacterial strain in the composition is in the range of $1×10^6$ to $1×10^{12}$ cfu/g or $1×10^6$ to $1×10^{12}$ cfu/ml.

6. The composition according to claim 2, which further contains 2'-fucosyllactose, and one or both of 3'-sialyllactose and lacto-N-tetraose.

7. A method for producing a composition comprising a spray-dried or lyophilized powder of a bacterial strain selected from the group consisting of:
   (a) *Bifidobacterium longum* subspecies *infantis* NITE BP-03068,
   (b) *Bifidobacterium bifidum* NITE BP-03058, and
   (c) *Bifidobacterium bifidum* NITE BP-03067;
   said method comprising:
   (i) culturing in a medium, to obtain a culture, a bacterial strain selected from the group consisting of:
      (a) *Bifidobacterium longum* subspecies *infantis* NITE BP-03068,
      (b) *Bifidobacterium bifidum* NITE BP-03058, and
      (c) *Bifidobacterium bifidum* NITE BP-03067; and
   (ii) spray-drying or lyophilizing the culture to obtain the spray-dried or lyophilized powder.

8. The spray-dried or lyophilized powder of claim 1, wherein the powder is spray-dried.

9. The spray-dried or lyophilized powder of claim 1, wherein the powder is lyophilized.

* * * * *